United States Patent [19]

Lee et al.

[11] Patent Number: 4,458,025

[45] Date of Patent: Jul. 3, 1984

[54] METHOD OF ZEOLITIC CATALYST MANUFACTURE

[75] Inventors: Bowman Lee, El Cerrito; Donald S. Santilli, Pinole, both of Calif.

[73] Assignee: Chevron Research Company, San Francisco, Calif.

[21] Appl. No.: 420,532

[22] Filed: Sep. 20, 1982

[51] Int. Cl.³ ............................................. B01J 29/10
[52] U.S. Cl. ..................................................... 502/66
[58] Field of Search ....................... 252/455 Z; 502/66

[56] References Cited

U.S. PATENT DOCUMENTS

| | | | |
|---|---|---|---|
| 3,321,521 | 5/1967 | Kerr ................................. | 252/455 Z |
| 3,326,818 | 6/1967 | Gladrow et al. ................ | 252/455 Z |
| 3,406,124 | 10/1968 | Eastwood et al. .............. | 252/455 Z |
| 3,428,550 | 2/1969 | Erickson et al. ................ | 252/455 Z |
| 3,929,668 | 12/1975 | Nelson et al. ................... | 252/455 Z |
| 3,945,943 | 3/1976 | Ward ................................ | 252/455 Z |
| 4,039,479 | 8/1977 | Gembicki et al. .............. | 252/455 Z |
| 4,046,713 | 9/1977 | Mitsche et al. ................. | 502/66 |
| 4,121,996 | 10/1978 | Hilfman ........................... | 506/66 X |

Primary Examiner—Carl F. Dees
Attorney, Agent, or Firm—S. R. LaPaglia; W. K. Turner; E. A. Schaal

[57] ABSTRACT

A method of making a new catalyst is disclosed which is useful for dehydrocyclizing alkanes. In this method, a non-acidic alumina sol is mulled with a zeolite to form a mixture, then the mixture is extruded and the resulting extrudate is dried, calcined, impregnated with a Group VIII metal, then dried and calcined again.

11 Claims, No Drawings

METHOD OF ZEOLITIC CATALYST MANUFACTURE

BACKGROUND OF THE INVENTION

The invention relates to a method of making a new catalyst which is useful in reforming hydrocarbons.

Catalytic reforming is well known in the petroleum industry and refers to the treatment of naphtha fractions to improve the octane rating by the production of aromatics. The more important hydrocarbon reactions occurring during reforming operation include dehydrogenation of cyclohexanes to aromatics, dehydroisomerization of alkylcyclopentanes to aromatics, and dehydrocyclization of acyclic hydrocarbons to aromatics. A number of other reactions also occur, including the following: dealkylation of alkylbenzenes, isomerization of paraffins, and hydrocracking reactions which produce light gaseous hydrocarbons, e.g., methane, ethane, propane and butane. Hydrocracking reactions are to be particularly minimized during reforming as they decrease the yield of gasoline boiling products.

Because of the demand for high octane gasoline for use as motor fuels, etc., extensive research is being devoted to the development of improved reforming catalysts and catalytic reforming processes. Catalysts for successful reforming processes must possess good selectivity, i.e., be able to produce high yields of liquid products in the gasoline boiling range containing large concentrations of high octane number aromatic hydrocarbons and accordingly, low yields of light gaseous hydrocarbons. The catalysts should possess good activity in order that the temperature required to produce a certain quality product need not be too high. It is also necessary that catalysts possess good stability in order that the activity and selectivity characteristics can be retained during prolonged periods of operation.

Catalysts comprising platinum, for example, platinum supported on alumina, are well known and widely used for reforming of naphthas. The most important products of catalytic reforming are benzene and alkylbenzenes. These aromatic hydrocarbons are of great value as high octane number components of gasoline.

Catalytic reforming is also an important process for the chemical industry because of the great and expanding demand for aromatic hydrocarbons for use in the manufacture of various chemical products such as synthetic fibers, insecticides, adhesives, detergents, plastics, synthetic rubbers, pharmaceutical products, high octane gasoline, perfumes, drying oils, ion-exchange resins, and various other products well known to those skilled in the art. One example of this demand is in the manufacture of alkylated aromatics such as ethylbenzene, cumene and dodecylbenzene by using the appropriate mono-olefins to alkylate benzene. Another example of this demand is in the area of chlorination of benzene to give chlorobenzene which is then used to prepare phenol by hydrolysis with sodium hydroxide. The chief use for phenol is in the manufacture of phenol-formaldehyde resins and plastics. Another route to phenol uses cumene as a starting material and involves the oxidation of cumene by air to cumene hydroperoxide which can then be decomposed to phenol and acetone by the action of an appropriate acid. The demand for ethylbenzene is primarily derived from its use to manufacture styrene by selective dehydrogenation; styrene is in turn used to make styrene-butadiene rubber and polystyrene. Ortho-xylene is typically oxidized to phthalic anhydride by reaction in vapor phase with air in the presence of a vanadium pentoxide catalyst. Phthalic anhydride is in turn used for production of plasticizers, polyesters and resins. The demand for para-xylene is caused primarily by its use in the manufacture of terephthalic acid or dimethylterephthalate which in turn is reacted with ethylene glycol and polymerized to yield polyester fibers. Substantial demand for benzene also is associated with its use to produce aniline, nylon, maleic anhydride, solvents and the like petrochemical products. Toluene, on the other hand, is not, at least relative to benzene and the $C_8$ aromatics, in great demand in the petrochemical industry as a basic building block chemical; consequently, substantial quantities of toluene are hydrodealkylated to benzene or disproportionated to benzene and xylene. Another use for toluene is associated with the transalkylation of trimethylbenzene with toluene to yield xylene.

Responsive to this demand for these aromatic products, the art has developed and industry has utilized a number of alternative methods to produce them in commercial quantities. One response has been the construction of a significant number of catalytic reformers dedicated to the production of aromatic hydrocarbons for use as feedstocks for the production of chemicals. As is the case with most catalytic processes, the principal measure of effectiveness for catalytic reforming involves the ability of the process to convert the feedstocks to the desired products over extended periods of time with minimum interference of side reactions.

The dehydrogenation of cyclohexane and alkylcyclohexanes to benzene and alkylbenzenes is the most thermodynamically favorable type of aromatization reaction of catalytic reforming. This means that dehydrogenation of cyclohexanes can yield a higher ratio of (aromatic product/nonaromatic reactant) than either of the other two types of aromatization reactions at a given reaction temperature and pressure. Moreover, the dehydrogenation of cyclohexanes is the fastest of the three aromatization reactions. As a consequence of these thermodynamic and kinetic considerations, the selectivity for the dehydrogenation of cyclohexanes is higher than that for dehydroisomerization or dehydrocyclization. Dehydroisomerization of alkylcyclopentanes is somewhat less favored, both thermodynamically and kinetically. Its selectivity, although generally high, is lower than that for dehydrogenation. Dehydrocyclization of paraffins is much less favored both thermodynamically and kinetically. In conventional reforming, its selectivity is much lower than that for the other two aromatization reactions.

The selectivity disadvantage of paraffin dehydrocyclization is particularly large for the aromatization compounds having a small number of carbon atoms per molecule. Dehydrocyclization selectivity in conventional reforming is very low for $C_6$ hydrocarbons. It increases with the number of carbon atoms per molecule, but remains substantially lower than the aromatization selectivity for dehydrogenation or dehydroisomerization of naphthenes having the same number of carbon atoms per molecule. A major improvement in the catalytic reforming process will require, above all else, a drastic improvement in dehydrocyclization selectivity that can be achieved while maintaining the adequate catalyst stability.

In the dehydrocyclization reaction, acyclic hydrocarbons are both cyclized and dehydrogenated to produce aromatics. The conventional methods of performing these dehydrocyclization reactions are based on the use of catalysts comprising a noble metal on a carrier. Known catalysts of this kind are based on alumina carrying 0.2% to 0.8% by weight of platinum and preferably a second auxiliary metal.

A disadvantage of most catalysts is that with $C_6$–$C_8$ paraffins, they are usually more selective for other reactions (such as hydrocracking) than they are for dehydrocyclization. A major advantage of the catalyst of the present invention is its high selectivity for dehydrocyclization.

The possibility of using carriers other than alumina has also been studied and it was proposed to use certain molecular sieves such as X and Y zeolites, which have pores large enough for hydrocarbons in the gasoline boiling range to pass through. However, catalysts based upon these molecular sieves have not been commercially successful.

In the conventional method of carrying out the aforementioned dehydrocyclization, acyclic hydrocarbons to be converted are passed over the catalyst, in the presence of hydrogen, at temperatures of the order of 500° C. and pressures of from 5 to 30 bars. Part of the hydrocarbons are converted into aromatic hydrocarbons, and the reaction is accompanied by isomerization and cracking reactions which also convert the paraffins into isoparaffins and lighter hydrocarbons.

The rate of conversion of the acyclic hydrocarbons into aromatic hydrocarbons varies with the number of carbon atoms per reactant molecule, reaction conditions and the nature of the catalyst.

The catalysts hitherto used have given moderately satisfactory results with heavy paraffins, but less satisfactory results with $C_6$–$C_8$ paraffins, particularly $C_6$ paraffins. Catalysts based on a type L zeolite are more selective with regard to the dehydrocyclization reaction; can be used to improve the rate of conversion to aromatic hydrocarbons without requiring higher temperatures than those dictated by thermodynamic considerations (higher temperatures usually have a considerable adverse effect on the stability of the catalyst); and produce excellent results with $C_6$–$C_8$ paraffins, but catalysts based on type L zeolite have not achieved commercial usage, apparently because of inadequate stability.

In one method of dehydrocyclizing aliphatic hydrocarbons, hydrocarbons are contacted in the presence of hydrogen with a catalyst consisting essentially of a type L zeolite having exchangeable cations of which at least 90% are alkali metal ions selected from the group consisting of ions of lithium, sodium, potassium, rubidium and cesium and containing at least one metal selected from the group which consists of metals of Group VIII of the Periodic Table of Elements, tin and germanium, said metal or metals including at least one metal from Group VIII of said Periodic Table having a dehydrogenating effect, so as to convert at least part of the feedstock into aromatic hydrocarbons.

To be used commercially, the catalyst is formed into pellets. These pellets have sufficient strength so that they will not disintegrate in the reactor. Inorganic oxides, such as silica and alumina, are often used as binders to give strength to the pellets, but these inorganic oxides have an adverse effect on catalyst selectivity.

SUMMARY OF THE INVENTION

The present invention is based in part on the discovery that a strong catalyst can be formed having a high activity and selectivity for the aromatization reaction by using as a binder a non-acidic alumina sol such as one which has been peptized with an acid, such as nitric acid, back-neutralized with a base, such as potassium hydroxide and washed. One preferred alumina is an alphaalumina monohydroxide. Another method of forming the non-acidic alumina sol is by peptizing the alumina with KOH to form potassium aluminate species. The strong catalyst is formed by mulling the alumina sol with a zeolite to form a mixture; extruding the mixture to form an extrudate; drying the calcining the extrudate; impregnating the calcined extrudate with a Group VIII metal (preferably platinum) to form a catalyst; and drying and calcining the catalyst. Preferably, the first calcination step is carried out at a temperature of about 1000° F. for from 1 to 2 hours, and the second calcination step is carried out at a temperature of 500° F. for about 2 hours.

DESCRIPTION OF THE PREFERRED EMBODIMENTS

In its broadest aspect, the present invention is based on the discovery that a strong zeolitic catalyst having a high activity and a high selectivity for aromatization can be made using a non-acidic alumina sol prepared either by peptizing the alumina with acid, followed by back-neutralization and a washing to remove any salts present; or by peptizing the alumina with a base to form alkali aluminates. This catalyst is formed by mulling together a zeolite and the non-acidic alumina sol, then extruding the mixture of zeolite and alumina sol to form an extrudate, drying and calcining the extrudate, impregnating the calcined extrudate with a Group VIII metal to form a catalyst, then drying and calcining the catalyst.

In the first embodiment, the alumina is peptized with acid to form a sol. Preferably, the alumina is peptized with nitric acid.

After the alumina sol has been peptized, it is essential that the alumina sol be back-neutralized to neutrality. This back-neutralization can be achieved using any basic solution, but, preferably, the basic solution is potassium hydroxide. If the alumina sol is not back-neutralized after peptization, then the selectivity of the resulting catalyst suffers greatly. Then the back-neutralized sol is washed to remove any salts.

In another embodiment, the non-acidic alumina sol is formed by peptizing the alumina with a base, such as potassium hydroxide. If this is done, no back-neutralization and wash is needed.

The zeolite and alumina are mulled together, and the resulting mixture is extruded to form an extrudate. One way to extrude the mixture is by controlling the moisture level so that a thick paste is formed. This is then forced through a circular dye to yield the catalyst pellet.

The extrudate is dried and calcined to add strength to the resulting catalyst. This first calcination step should be at about 1000° F. for from 1 to 2 hours. The high temperature is necessary to get proper strength in the resulting catalyst.

After the extrudate has been calcined, it is impregnated with a Group VIII metal to form a catalyst. Preferably, the Group VIII metal is platinum, and preferably the platinum is impregnated in the extrudate using a 1% molar solution of $Pt(NH_3)_4(NO_3)_2$. The zeolite is impregnated after it has been formed into an extrudate because, if the zeolite is impregnated before the zeolite is formed into the extrudate, then the high calcination temperatures of the first calcination step would cause the platinum to sinter unless the oxygen concentration is kept low.

Then the catalyst is dried and calcined in air in order to make $PtO_2$. This also helps platinum dispersion. In this second calcination, the temperature should be about 500° F. instead of the 1000° F. used in the first calcination. This is because higher calcination temperatures would cause the platinum on the catalyst to sinter.

The term "selectivity" as used in the present invention is defined as the weight percent aromatics formed from acyclic hydrocarbons relative to weight percent converted to aromatics and cracked products, $$\text{i.e., Selectivity} = \frac{100 \times \text{weight percent of aromatics}}{\text{weight percent of aromatics and cracked products}}$$

Isomerization of paraffins and interconversion of paraffins and alkylcyclopentanes having the same number of carbon atoms per molecule are not considered in determining selectivity.

The selectivity for converting acyclic hydrocarbons to aromatics is a measure of the efficiency of the process in converting acyclic hydrocarbons to the desired and valuable products: aromatics and hydrogen, as opposed to the less desirable products of hydrocracking.

Highly selective catalysts produce more hydrogen than less selective catalysts because hydrogen is produced when acyclic hydrocarbons are converted to aromatics and hydrogen is consumed when acyclic hydrocarbons are converted to cracked products. Increasing the selectivity of the process increases the amount of hydrogen produced (more aromatization) and decreases the amount of hydrogen consumed (less cracking).

Another advantage of using highly selective catalysts is that the hydrogen produced by highly selective catalysts is purer than that produced by less selective catalysts. This higher purity results because more hydrogen is produced, while less low boiling hydrocarbons (cracked products) are produced. The purity of hydrogen produced in reforming is critical if, as is usually the case in an integrated refinery, the hydrogen produced is utilized in processes such as hydrotreating and hydrocracking, which require at least certain minimum partial pressures of hydrogen. If the purity becomes too low, the hydrogen can no longer be used for this purpose and must be used in a less valuable way, for example as fuel gas.

Feedstock

Regarding the acyclic hydrocarbons that can be converted to aromatics by the catalyst of the present invention, they are most commonly paraffins but can in general be any acyclic hydrocarbon capable of undergoing ring closure to produce an aromatic hydrocarbon. That is, the catalyst of the present invention is useful for the dehydrocyclization of any acyclic hydrocarbon capable of undergoing ring closure to produce an aromatic hydrocarbon and capable of being vaporized at the dehydrocyclization temperatures used herein. More particularly, suitable acyclic hydrocarbons include acyclic hydrocarbons containing 6 or more carbon atoms per molecule such as $C_6$–$C_{20}$ paraffins, and $C_6$–$C_{20}$ olefins. Specific examples of suitable acyclic hydrocarbons are: (1) paraffins such as n-hexane, 2-methylpentane, 3-methylpentane, n-heptane, 2-methylhexane, 3-methylhexane, 3-ethylpentane, 2,5-dimethylhexane, n-octane, 2-methylheptane, 3-methylheptane, 4-methylheptane, 3-ethylhexane, n-nonane, 2-methyloctane, 3-methyloctane, n-decane and the like compounds; and (2) olefins such as 1-hexene, 2-methyl-1-pentene, 1-heptene, 1-octene, 1-nonene and the like compounds.

Preferably, the feedstock is substantially free of sulfur, nitrogen, metals, and other known poisons for reforming catalysts. The feedstock can be made substantially free of sulfur, nitrogen, metals, and other known poisons by conventional hydrofining techniques.

In the case of a feedstock which is not already low in sulfur, acceptable levels can be reacted by hydrogenating the feedstock in a presaturation zone where the naphtha is contacted with a hydrogenation catalyst which is resistant to sulfur poisoning. A suitable catalyst for this hydrodesulfurization process is, for example, an alumina-containing support and a minor proportion of molybdenum oxide, cobalt oxide and/or nickel oxide. Hydrodesulfurization is ordinarily conducted at 315° C. to 455° C., at 200 to 2000 psig, and at a liquid hourly space velocity of 1 to 5. The sulfur and nitrogen contained in the naphtha are converted to hydrogen sulfide and ammonia, respectively, which can be removed prior to reforming by suitable conventional processes.

Dehydrocyclization Reaction

The catalyst of the present invention can be used to form aromatics by contacting acyclic hydrocarbons with the catalyst in a dehydrocyclization zone maintained at dehydrocyclization conditions. This contacting may be accomplished by using the catalyst in a fixed bed system, a moving bed system, a fluidized system, or in a batch-type operation; however, in view of the danger of attrition losses of the valuable catalyst and of well-known operational advantages, it is preferred to use either a fixed bed system or a dense-phase moving bed system. It is also contemplated that the contacting step can be performed in the presence of a physical mixture of particles of a conventional dual-function catalyst of the prior art. In a fixed bed system, the acyclic hydrocarbon-containing charge stock is preheated by any suitable heating means to the desired reaction temperature and then passed into a dehydrocyclization zone containing a fixed bed of the catalyst. It is, of course, understood that the dehydrocyclization zone may be one or more separate reactors with suitable means therebetween to ensure that the desired conversion temperature is maintained at the entrance to each reactor. It is also important to note that the reactants may be contacted with the catalyst bed in either upward, downward, or radial flow fashion with the latter being preferred. In addition, the reactants may be in a liquid phase, a mixed liquid-vapor phase, or a vapor phase when they contact the catalyst, with best results obtained in the vapor phase. The dehydrocyclization system then preferably comprises a dehydrocyclization zone containing one or more fixed beds or dense-phase moving beds of the catalyst. In a multiple bed system, the present catalyst may be used in less than all of the beds with a conventional dual-function catalyst being used in the remainder of the beds. The dehydrocyclization zone may be one or more separate reactors with suitable heating means therebetween to compensate for the endothermic nature of the dehydrocyclization reaction that takes place in each catalyst bed.

Although hydrogen is the preferred diluent for use in the subject dehydrocyclization method, in some cases other art-recognized diluents may be advantageously utilized, either individually or in admixture with hydrogen, such as $C_1$ to $C_5$ paraffins such as methane, ethane, propane, butane and pentane; the like diluents, and mixtures thereof. Hydrogen is preferred because it serves the dual function of not only lowering the partial pressure of the acyclic hydrocarbon, but also of suppressing the formation of hydrogen-deficient, carbonaceous deposits (commonly called coke) on the catalytic composite. Ordinarily, hydrogen is utilized in amounts sufficient to insure a hydrogen to hydrocarbon mole ratio of about 0 to about 20:1, with best results obtained in the range of about 2:1 to about 6:1. The hydrogen charged to the dehydrocyclization zone will typically be contained in a hydrogen-rich gas stream recycled from the effluent stream from this zone after a suitable gas/liquid separation step.

The hydrocarbon dehydrocyclization conditions used include a reactor pressure which is selected from the range of about 1 atmosphere to about 500 psig, with the preferred pressure being about 50 psig to about 200 psig. The temperature of the dehydrocyclization is preferably about 450° C. to about 550° C. As is well known to those skilled in the dehydrocyclization art, the initial selection of the temperature within this broad range is made primarily as a function of the desired conversion level of the acyclic hydrocarbon considering the characteristics of the charge stock and of the catalyst. Ordinarily, the temperature then is thereafter slowly increased during the run to compensate for the inevitable deactivation that occurs to provide a relatively constant value for conversion.

The liquid hourly space velocity (LHSV) used is selected from the range of about 0.1 to about 10 hr.$^{-1}$, with a value in the range of about 0.3 to about 5 hr.$^{-1}$ being preferred.

Reforming generally results in the production of hydrogen. Thus, exogenous hydrogen need not necessarily be added to the reforming system except for pre-reduction of the catalyst and when the feed is first introduced. Generally, once reforming is underway, part of the hydrogen produced is recirculated over the catalyst. The presence of hydrogen serves to reduce the formation of coke which tends to poison the catalyst. Hydrogen is preferably introduced into the reforming reactor at a rate varying from 0 to about 20 moles of hydrogen per mole of feed. The hydrogen can be in admixture with light gaseous hydrocarbons.

If, after a period of operation, the catalyst has become deactivated by the presence of carbonaceous deposits, said deposits can be removed from the catalyst by passing an oxygen-containing gas, such as air, into contact with the catalyst at an elevated temperature in order to burn the carbonaceous deposits from the catalyst. The method of regenerating the catalyst will depend on whether there is a fixed bed, moving bed, or fluidized bed operation. Regeneration methods and conditions are well known in the art.

The Catalyst

The catalyst of the present invention is made by forming a non-acidic alumina sol; mulling the alumina sol with a zeolite to form a mixture; extruding the mixture to form an extrudate; drying and calcining the extrudate; impregnating the calcined extrudate with a Group VIII metal to form a catalyst; then drying and calcining the catalyst. Preferably, the zeolite is ion-exchanged after the extrudate is calcined, but prior to impregnation with platinum.

The alumina used in the present invention is preferably an alpha-alumina monohydrate. The alpha-alumina monohydrate used in the present invention is available from a variety of commercial sources. It may also be prepared by partially dehydrating trihydrated alumina by conventional methods. Alpha-alumina monohydrate may be conveniently prepared by precipitation from a hot alum solution by combination with ammonia or sodium aluminate solutions (see, for example, J. A. Lewis and C. A. Taylor, "J. App. Chem.", Vol. 8, 1958, and H. Lehl, "J. Phys. Chem.", Vol. 40, 1936). A preferred source is alpha-alumina monohydrate produced from the hydrolysis of an aluminum alkoxide [Al(OR)$_3$, where R is the same or different and is an alkyl group].

The catalyst according to the invention is a large-pore zeolite charged with one or more dehydrogenating constituents. The term "large-pore zeolite" is defined as a zeolite having an effective pore diameter of 6 to 15 Angstroms.

Among the large-pored crystalline zeolites which have been found to be useful in the practice of the present invention, type L zeolite, zeolite X, zeolite Y and faujasite are the most important and have apparent pore sizes on the order of 7 to 9 Angstroms.

The chemical formula for zeolite Y expressed in terms of mole oxides may be written as:

$$(0.7-1.1)Na_2O:Al_2O_3:xSiO_2:yH_2O$$

wherein x is a value greater than 3 up to about 6 and y may be a value up to about 9. Zeolite Y has a characteristic X-ray powder diffraction pattern which may be employed with the above formula for identification. Zeolite Y is described in more detail in U.S. Pat. No. 3,130,007. U.S. Pat. No. 3,130,007 is hereby incorporated by reference to show a zeolite useful in the present invention.

Zeolite X is a synthetic crystalline zeolitic molecular sieve which may be represented by the formula:

$$(0.7-1.1)M_{2/n}O:Al_2O_3:(2.0-3.0)SiO_2:yH_2O$$

wherein M represents a metal, particularly alkali and alkaline earth metals, n is the valence of M, and y may have any value up to about 8 depending on the identity of M and the degree of hydration of the crystalline zeolite. Zeolite X, its X-ray diffraction pattern, its properties, and method for its preparation are described in detail in U.S. Pat. No. 2,882,244. U.S. Pat. No. 2,882,244 is hereby incorporated by reference to show a zeolite useful in the present invention.

The preferred catalyst according to the invention is a type L zeolite charged with one or more dehydrogenating constituents.

Type L Zeolite

Type L zeolites are synthetic zeolites. A theoretical formula is $M_{9/n}[(AlO_2)_9(SiO_2)_{27}]$ in which M is a cation having the valency n.

The real formula may vary without changing the crystalline structure; for example, the mole ratio of silicon to aluminum (Si/Al) may vary from 1.0 to 3.5.

Although there are a number of cations that may be present in zeolite L, in one embodiment, it is preferred to synthesize the potassium form of the zeolite, i.e., the form in which the exchangeable cations present are substantially all potassium ions. The reactants accordingly employed are readily available and generally water soluble. The exchangeable cations present in the zeolite may then conveniently be replaced by other exchangeable cations, as will be shown below, thereby yielding isomorphic form of zeolite L.

In one method of making zeolite L, the potassium form of zeolite L is prepared by suitably heating an aqueous metal aluminosilicate mixture whose composition, expressed in terms of the mole ratios of oxides, falls within the range:

| | |
|---|---|
| $K_2O/(K_2O + Na_2O)$ | From about 0.33 to about 1 |
| $(K_2O + Na_2O)/SiO_2$ | From about 0.35 to about 0.5 |
| $SiO_2/Al_2O_3$ | From about 10 to about 28 |
| $H_2O/(K_2O + Na_2O)$ | From about 15 to about 41 |

The desired product is hereby crystallized out relatively free from zeolites of dissimilar crystal structure.

The potassium form of zeolite L may also be prepared in another method along with other zeolitic compounds by employing a reaction mixture whose composition, expressed in terms of mole ratios of oxides, falls within the following range:

| | |
|---|---|
| $K_2O/(K_2O + Na_2O)$ | From about 0.26 to 1 |
| $(K_2O + Na_2O)/SiO_2$ | From about 0.34 to about 0.5 |
| $SiO_2/Al_2O_3$ | From about 15 to about 28 |
| $H_2O/(K_2O + Na_2O)$ | From about 15 to 51 |

It is to be noted that the presence of sodium in the reaction mixture is not critical to the present invention. However, it has been found that the potassium form of zeolite L is more readily obtained from reaction mixtures in which sodium is incorporated within the range indicated above.

When the zeolite is prepared from reaction mixtures containing sodium, sodium ions are generally also included within the product as part of the exchangeable cations together with the potassium ions. The product obtained from the above ranges has a composition, expressed in terms of moles of oxides, corresponding to the formula:

$0.9-1.3[(1-x)K_2O, xNa_2O]:Al_2O_3:5.2-6.9SiO_2:yH_2O$ wherein "x" may be any value from 0 to about 0.75 and "y" may be any value from 0 to about 9.

In making zeolite L, representative reactants are activated alumina, gamma alumina, alumina trihydrate and sodium aluminate as a source of alumina. Silica may be obtained from sodium or potassium silicate, silica gels, silicic acid, aqueous colloidal silica sols and reactive amorphous solid silicas. The preparation of typical silica sols which are suitable for use in the process of the present invention are described in U.S. Pat. Nos. 2,574,902 and 2,597,872. Typical of the group of reactive amorphous solid silicas, preferably having an ultimate particle size of less than 1 micron, are such materials as fume silicas, chemically precipitated and precipitated silica sols. Potassium and sodium hydroxide may supply the metal cation and assist in controlling pH.

In making zeolite L, the usual method comprises dissolving potassium or sodium aluminate and alkali, viz., potassium or sodium hydroxide, in water. This solution is admixed with a water solution of sodium silicate, or preferably with a water-silicate mixture derived at least in part from an aqueous colloidal silica sol. The resultant reaction mixture is placed in a container made, for example, of metal or glass. The container should be closed to prevent loss of water. The reaction mixture is then stirred to insure homogeneity.

The zeolite may be satisfactorily prepared at temperatures of from about 90° C. to 200° C. the pressure being atmospheric or at least that corresponding to the vapor pressure of water in equilibrium with the mixture of reactants at the higher temperature. Any suitable heating apparatus, e.g., an oven, sand bath, oil bath or jacketed autoclave, may be used. Heating is continued until the desired crystalline zeolite product is formed. The zeolite crystals are then filtered off and washed to separate them from the reactant mother liquor. The zeolite crystals should be washed, preferably with distillated water, until the effluent wash water, in equilibrium with the product, has a pH of between about 9 and 12. As the zeolite crystals are washed, the exchangeable cation of the zeolite may be partially removed and is believed to be replaced by hydrogen cations. If the washing is discontinued when the pH of the effluent wash water is between about 10 and 11, the $(K_2O+Na_2O)/Al_2O_3$ molar ratio of the crystalline product will be approximately 1.0. Thereafter, the zeolite crystals may be dried, conveniently in a vented oven.

Zeolite L has been characterized in "Zeolite Molecular Sieves" by Donald W. Breck, John Wiley & Sons, 1974, as having a framework comprising 18 tetrahedra unit cancrinite-type cages linked by double 6-rings in columns and crosslinked by single oxygen bridges to form planar 12-membered rings. These 12-membered rings produce wide channels parallel to the c-axis with no stacking faults. Unlike erionite and cancrinite, the cancrinite cages are symmetrically placed across the double 6-ring units. There are four types of cation locations: A in the double 6-rings, B in the cancrinite-type cages, C between the cancrinite-type cages, and D on the channel wall. The cations in site D appear to be the only exchangeable cations at room temperature. During dehydration, cations in site D probably withdraw from the channel walls to a fifth site, site E, which is located between the A sites. The hydrocarbon sorption pores are approximately 7 to 8 Angstroms in diameter.

A more complete description of these zeolites is given, e.g., in U.S. Pat. No. 3,216,789 which, more particularly, gives a conventional description of these zeolites, U.S. Pat. No. 3,216,789 is hereby incorporated by reference to show a type L zeolite useful in the present invention.

Various factors have an effect on the X-ray diffraction pattern of a zeolite. Such factors include temperature, pressure, crystal size, impurities, and type of cations present. For instance, as the crystal size of the type L zeolite becomes smaller, the X-ray diffraction pattern becomes broader and less precise. Thus, the term "zeolite L" includes any zeolites made up of cancrinite cages having an X-ray diffraction pattern substantially similar to the X-ray diffraction patterns shown in U.S. Pat. No. 3,216,789.

Crystal size also has an effect on the selectivity of the catalyst. For reasons not yet fully understood, catalysts having at least 80% of the crystals of the type L zeolite larger than 1000 Angstroms give longer run length than catalysts having substantially all of the crystals of the type L zeolite between 200 and 500 Angstroms. Thus, large crystal-size type L zeolite is the preferred support.

Type L zeolites are conventionally synthesized largely in the potassium form, i.e., in the theoretical formula given previously, most of the M cations are potassium. The M cations are exchangeable, so that a given type L zeolite, e.g., a type L zeolite in the potassium form, can be used to obtain type L zeolites containing other cations, by subjecting the type L zeolite to ion exchange treatment in an aqueous solution of appropriate salts. However, it is difficult to exchange all of the original cations, e.g., potassium, since some exchangeable cations in the zeolite are in sites which are difficult for the reagents to reach.

Group VIII Metals

The catalysts according to the invention are charged with one or more Group VIII metals, e.g., nickel, ruthenium, rhodium, palladium, iridium or platinum.

The preferred Group VIII metals are iridium and particularly platinum, which are more selective with regard to dehydrocyclization and are also more stable under the dehydrocyclization reaction conditions than other Group VIII metals.

The preferred percentage of platinum in the catalyst is between 0.1% and 5%, more preferably from 0.1% to 1.5%.

Group VIII metals are introduced into the L zeolite by synthesis, impregnation or exchange in an aqueous solution of an appropriate salt. When it is desired to introduce two Group VIII metals into the zeolite, the operation may be carried out simultaneously or sequentially.

By way of example, platinum can be introduced by impregnating the zeolite with an aqueous solution of tetramminoplatinum (II) nitrate, tetramminoplatinum (II) hydroxide, dinitrodiamino-platinum or tetramminoplatinum (II) chloride. In an ion exchange process, platinum can be introduced by using cationic platinum complexes such as tetramminoplatinum (II) nitrate.

Alkaline Earth Metals

A possible additional component of the present catalyst is an alkaline earth metal. That alkaline earth metal can be either barium, strontium or calcium. Preferably, the alkaline earth metal is barium. The alkaline earth metal can be incorporated into the zeolite by synthesis, impregnation or ion exchange. Barium is preferred to the other alkaline earths because the resulting catalyst has high activity, high selectivity and high stability.

In one embodiment, at least part of the alkali metal is exchanged with barium, using techniques known for ion exchange of zeolites. This involves contacting the zeolite with a solution containing excess $Ba^{++}$ ions. The barium should preferably constitute from 0.1% to 35% of the weight of the zeolite, more preferably from 1% to 20% by weight.

At this stage the catalyst is ready for use in the dehydrocyclization process. In some cases however, for example when the metal or metals have been introduced by an ion exchange process, it is preferable to eliminate any residual acidity of the zeolite by treating the catalyst with an aqueous solution of a salt of a suitable alkali or alkaline earth element in order to neutralize any hydrogen ions formed during the reduction of metal ions by hydrogen.

In order to obtain optimum selectivity, temperature should be adjusted so that reaction rate is appreciable, but conversion is less than 98%, as excessive temperature and excess reaction can have an adverse affect on selectivity. Pressure should also be adjusted within a proper range. Too high a pressure will place a thermodynamic (equilibrium) limit on the desired reaction, especially for hexane aromatization, and too low a pressure may result in coking and deactivation.

Although the primary benefit of this invention is in improving the selectivity for conversion of acyclic hydrocarbons (especially $C_6$–$C_8$ paraffins) to aromatics, it is also surprisingly found that the selectivity for conversion of methylcyclopentane to benzene is excellent. This reaction, which on conventional reforming catalysts based on chlorided alumina involves an acid catalyzed isomerization step, occurs on the catalyst of this invention with selectivity as good as or better than on the chlorided alumina based catalysts of the prior art. Thus, the present catalyst can also be used to catalyze the conversion of stocks high in 5-membered-ring alkyl naphthenes to aromatics.

Another advantage of this catalyst is that it is more stable than prior art zeolitic catalysts. Stability of the catalyst, or resistance to deactivation, determines its useful run length. Longer run lengths result in less down time and expense in regenerating or replacing the catalyst charge.

The bound zeolite can be washed with aqueous salt solution to assure that the proper amount of alkali or barium is present to make an active and selective catalyst. Too much alkali reduces catalyst life while too little results in a more acidic catalyst, which lowers the selectivity.

EXAMPLES

The invention will be further illustrated by the following examples which set forth a particularly advantageous method and composition embodiments. While the examples are provided to illustrate the present invention, they are not intended to limit it.

EXAMPLE 1

Silica Bound Catalyst 0.5 gram sodium stabilized Ludox (30% solid) and 0.5 gram potassium-L zeolite were mulled together, dried, and calcined (1000° F.). 1 wt. % Pt [Pt(NH$_3$)$_4$(NO$_3$)$_2$] relative to potassium-L zeolite was impregnated and this was dried and calcined (500° F., 2 hours). This catalyst was run in the reactor test. The results are in the Table.

EXAMPLE 2

Aluminum Based Catalyst 1 gram Al$_2$O$_3$ sol (22% solid) and 0.5 gram potassium-L zeolite were mulled together, dried, and calcined (1000° F.), Pt was added as in Example 1 and the reactor test results are given in the Table. (Al$_2$O$_3$ sol preparation: 113 grams catapal blended with 375 ml H$_2$O for 1 minute, 12 grams 70% nitric acid added, this was blended for 1 minute, poured into a jar, and allowed to gel.)

EXAMPLE 3

Neutralized $Al_2O_3$ Bound Catalyst

This was made in the same way as the catalyst in Example 2 except the $Al_2O_3$ sol was neutralized by adding enough KOH dissolved in a minimum amount of $H_2O$ to neutralize the $HNO_3$. The reactor test results are given in the Table.

EXAMPLE 4

KOH Peptized $Al_2O_3$ Bound Catalyst

This catalyst was made in the same way as the catalyst in Example 2 except the $Al_2O_3$ was peptized with KOH instead of $KNO_3$. The reactor test results are given in the Table.

TABLE

Reactor Test Results For Examples 1–4[1]

| | Wt. % Bz | Selectivity |
|---|---|---|
| Example 1 | 27 | 76 |
| Example 2 | 32 | 37 |
| Example 3 | 28 | 72 |
| Example 4 | 43 | 78 |

[1]Test conditions: 880° F., 125 psi $H_2$ at 20 ml/minute (atm), 1 ml/hour $NC_6$ feed.

While the present invention has been described with reference to specific embodiments, this application is intended to cover those various changes and substitutions which may be made by those skilled in the art without departing from the spirit and scope of the appended claims.

What is claimed is:

1. A method of forming a catalyst comprising:
   (a) forming a non-acidic alumina sol;
   (b) mulling said alumina sol with a zeolite to form a mixture;
   (c) extruding said mixture to form an extrudate;
   (d) drying said extrudate;
   (e) calcining said dried extrudate;
   (f) impregnating said calcined extrudate with a Group VIII metal to form a catalyst;
   (g) drying said catalyst; and
   (h) calcining said dried catalyst.

2. A method of forming a catalyst according to claim 1 wherein said non-acidic alumina sol is formed by peptizing an alumina, back-neutralizing said peptized alumina sol and washing said sol.

3. A method of forming a catalyst according to claim 2 wherein said alumina sol is an alpha-alumina monohydrate sol.

4. A method of forming a catalyst according to claim 2 wherein said alumina is peptized with nitric acid.

5. A method of forming a catalyst according to claim 2 wherein said alumina sol is back-neutralized with potassium hydroxide.

6. A method of forming a catalyst according to claim 1 wherein said non-acidic sol is formed by peptizing alumina with potassium hydroxide.

7. A method of forming a catalyst according to claim 1 wherein said zeolite is a potassium-type L zeolite.

8. A method of forming a catalyst according to claim 1 wherein said calcining in step (e) is conducted at a temperature of about 1000° F. for from 1 to 2 hours.

9. A method of forming a catalyst according to claim 1 wherein said Group VIII metal is platinum.

10. A method of forming a catalyst according to claim 1 wherein said impregnation of said calcined extrudate is conducted with a 1% molar solution of $Pt(NH_3)_4(NO_3)_2$.

11. A method of forming a catalyst according to claim 1 wherein said calcining in step (h) is conducted at about 500° F. for about 2 hours.

* * * * *